United States Patent
Abu-Mostafa (10) Patent No.: US 12,220,282 B2
(45) Date of Patent: Feb. 11, 2025

(54) ULTRASOUND DETECTION OF CLOTS IN THE BLOODSTREAM

(71) Applicant: CALIFORNIA INSTITUTE OF TECHNOLOGY, Pasadena, CA (US)

(72) Inventor: Yaser S. Abu-Mostafa, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 166 days.

(21) Appl. No.: 17/880,189

(22) Filed: Aug. 3, 2022

(65) Prior Publication Data

US 2023/0042474 A1 Feb. 9, 2023

Related U.S. Application Data (60) Provisional application No. 63/229,342, filed on Aug. 4, 2021.

(51) Int. Cl.
*A61B 8/08* (2006.01)
*A61B 8/00* (2006.01)

(52) U.S. Cl.
CPC ............ *A61B 8/5223* (2013.01); *A61B 8/085* (2013.01); *A61B 8/488* (2013.01); *A61B 8/5207* (2013.01)

(58) Field of Classification Search
CPC ....... A61B 8/5223; A61B 8/085; A61B 8/488; A61B 8/5207; A61B 8/06
See application file for complete search history.

(56) References Cited

U.S. PATENT DOCUMENTS

| 5,348,015 A | 9/1994 | Moehring et al. |
| 6,196,972 B1 * | 3/2001 | Moehring ............ A61B 8/0816 600/441 |
| 2009/0204338 A1 | 8/2009 | Nielsen et al. |
| 2010/0069757 A1 | 3/2010 | Yoshikawa et al. |
| 2014/0243614 A1 * | 8/2014 | Rothberg ............... A61B 5/318 600/407 |
| 2015/0025380 A1 | 1/2015 | Azegami et al. |
| 2016/0157814 A1 | 6/2016 | Palanisamy et al. |

OTHER PUBLICATIONS

International Search Report and Written Opinion for Application No. PCT/US2022/039297, mailed on Dec. 22, 2022, 14 pages.

\* cited by examiner

*Primary Examiner* — Peter Luong
(74) *Attorney, Agent, or Firm* — Sheppard Mullin Richter & Hampton LLP (57) ABSTRACT

Systems and methods disclosed herein relate to the detection of irregular particles in a blood flow based on a determined relative speed of a particle suspended in a blood flow and/or other properties of a particle suspended in a blood flow including a particle's relative position within a blood vessel and a particles tendency to cluster with other particles suspended in a blood flow. Based on a determined relative speed and/or other relevant factors, the properties of irregular particles may also be measured, including the size, shape, and frequency of irregular particles in a blood flow. Machine learning techniques may be employed to determine patterns for the behavior of irregular particles suspended in a blood flow. These patterns may correspond to particular health risks and conditions.

20 Claims, 6 Drawing Sheets

ULTRASOUND DETECTION OF CLOTS IN THE BLOODSTREAM

RELATED APPLICATION

This application claims the benefit of U.S. Provisional Application No. 63/229,342 filed on Aug. 4, 2021, the content of which is incorporated herein by reference in its entirety.

TECHNICAL FIELD

The present disclosure relates generally to the detection and analysis of objects in the bloodstream via ultrasound. In particular, some implementations may relate to early, pre-symptomatic detection and analysis of objections, including blood clots, using machine learning.

BACKGROUND

Abnormalities in the bloodstream can pose serious health risks. Irregular object and formations in the bloodstream, including blood clots, can be particularly dangerous. Some objects, like clots, gradually become larger over time. As clots and other objects in the bloodstream become larger, blood flow becomes more and more restricted which increases the risk of serious health conditions such as stroke, pulmonary embolism, deep vein thrombosis, and other conditions. Presently, medical technology only enables detection of clots and other objects that are large enough to be observed directly using imaging technology such as ultrasound or computed tomography (CT) By the time these objects and clots are large enough to detect, patients are likely already experiencing symptoms and other adverse health outcomes. Therefore, detection of small objects and clots is desirable because it would enable doctors to identify and treat conditions early, before patients begin experiencing adverse health outcomes.

SUMMARY

Systems and methods are described herein for the detection of particles in a bloodstream, such as blood clots, based on the relative speed of the particles compared to the speed of the bloodstream. In addition to the relative speed, detection may also be accomplished and/or assisted by examining the relative position of particles and blood clots within the cross section of a blood vessel and the position of blood clots in a blood vessel relative to each other. Changes in both the speed and the position of particles are detectable when solid particles are moving in a fluid. These speed and position parameters are affected by the size, shape, and other properties of the particles.

An ultrasound sensor may be used to accomplish the above described detection. In an embodiment, the ultrasound sensor may be used with color Doppler for the detection. The color Doppler technique uses pulse-wave Doppler with short pulses to create an image sequence of blood flow in a target region of a blood vessel. The image may contain information about the presence and properties of particles, including blood clots, suspended in the bloodstream.

Machine learning may be used to extract the relevant information from an image sequence of a blood flow. A machine learning model may be trained using collected data comprising sample image sequences of blood flows and known targets. Known targets may be the confirmed size or frequency of a particle or blood clot in a particular sample. Known targets may also be other parameters. In an embodiment, a known target may be the risk that a clot will cause a particular health problem within a particular time frame. In an embodiment, the machine learning model may be a neural network.

Other features and aspects of the disclosure will become apparent from the following detailed description, taken in conjunction with the accompanying drawings, which illustrate, by way of example, the features in accordance with various embodiments. The summary is not intended to limit the scope of the invention, which is defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION

Early detection of clots and/or other abnormalities in the blood stream can save lives. The systems and methods disclosed herein are directed to the detection of clots and other particles in the bloodstream including detection of their frequency, size, relative position within a blood vessel, and other properties. The systems and methods employed non-invasive methods wherein clots and other particles can be detected based on their observed fluid mechanics behavior. Clots and other particles having a diameter of around 90 microns may be detected with the systems and methods described herein.

The technology is grounded in an important fluid mechanics principle—particles traveling in a fluid do not travel at the same speed as the fluid itself under certain conditions. The speed of individual particles suspended within a fluid depends on the size of the particle and other factors. Therefore, movement of these particles within the fluid causes a change in the frequency of a wave relative to the speed of the fluid. These changes in wave frequency can be detected and mapped back to the existence, size, and frequency of particles within a fluid. This is known as a Doppler shift.

The Navier-Stokes and Newton-Euler equations are two sets of important equations that interact with each other and together describe the flow of a fluid that contains solid particles. The Navier Stokes equations describe the flow of a fluid:

$$\nabla \cdot u_f = 0$$

$$\frac{\partial u_f}{\partial t} + u_f \cdot \nabla u_f = -\frac{1}{\rho_f}\nabla p + v\nabla^2 u_f$$

where $u_f, \rho_f, p$ and $v=\mu/\rho_f$ are the fluid velocity, density, pressure and kinematic viscosity and $\mu$ is the dynamic viscosity.

When solid objects or particles are suspended in and moving within a fluid, the Navier-Stokes must be combined with other equations that describe the motion of the suspended particles. The Newton-Euler equations describe the motion of such particles:

$$\rho_p V_p \frac{du_p}{dt} = \oint_{\partial V_p} \sigma \cdot n dS + (\rho p - \rho f)Vpg + Fc$$

$$I_p \frac{d\omega_p}{dt} = \oint_{\partial V_p} r \times \sigma \cdot n dS + Tc$$

where Vp=4πa3/3 and Ip=2ρpVpa2/5 are the particle volume and moment of inertia, with a the particle radius; g is the gravitational acceleration; σ=−pI+2 μE is the fluid stress, with I the identity matrix and E=(∇uf+∇uTf)/2 the deformation tensor; r is the distance vector from the center of the sphere while n is the unit vector normal to the particle surface ∂Vp, and Fc and Tc represent additional forces and torques acting on the particles.

An important parameter for these equations is the Reynolds number. The Reynolds number associated with a fluid describes the way the fluid behaves including characteristics such as inertial and viscous forces in the flow. In a laminar flow, particles do travel at the same speed as the fluid if the Reynolds number is less than 1. There is a differential in speed, however, when the Reynolds number exceeds the threshold of 1. The Reynolds number of the fluid itself is typically denoted Re. However, the flow around a particular particle suspended within the fluid has its own Reynolds number, denoted Re_p. The Re_p effects a differential in speed between the particle and the fluid in which the particle is suspended. This may be referred to in the art as "slip." In addition to the speed differential, particles moving in a fluid may also move between the center and walls of the fluid flow and may prefer to cluster together within the fluid flow.

The Reynolds number for an average blood flow is approximately 2,000. Therefore, because the Reynolds number for blood is three orders of magnitude greater than the threshold of 1, it is possible to detect the differential speed of particles moving within a blood flow. This detection can be accomplished by imaging a blood flow using ultrasound Doppler techniques. Each particle or clot moving in the bloodstream is an "event" that will stay within the range of the ultrasound sensor only for a short time as the blood carries it away. Color Doppler may be used to image a blood flow. Additionally, the magnitude and frequency of an observable Doppler shift would also depend on the size of the particle or blood clot. Therefore, a Doppler signal may reveal multiple pieces of information about particles in the blood. For instance, it may reveal not only their existence but also properties such as frequency, size, position, and other factors. These additional factors may assist in distinguishing clots and other factors from noise.

Clots and other particles in the bloodstream can be detected because they behave differently from the regular cells making up the blood stream. Clots and other particles exhibit distinguishable fluid mechanics behavior. Namely, clots and other particles moving in the blood stream travel at a different speeds than the surrounding blood stream. Clots and other particles also have a tendency to occupy particular positions within a blood vessel as well as particular positions relative to each other. These three behavior patterns, (i) differential speed, (ii) relative position within the blood vessel, and (iii) relative position to other particles in the blood flow, provide for the detection of clots and their properties.

Individual clots or other particles moving in a bloodstream will appear as "events" in the Doppler spectrum as they pass through the range of an ultrasound probe. Measuring the Doppler shift relative to the frequency of the blood flow in the portion of the imaged blood vessel provides a strong reference point. In other words, the Doppler shift is measured relative to a central frequency. Therefore, the presence of a clot or other particle moving in the blood flow can still be detected with a high level of confidence even if there are variations in the blood flow. For instance, changes in the blood flow may be present depending on which portion of a blood vessel is measured within a patient, whether the patients has eaten recently, and other factors. The clot detection is also reliable in different patients who may have differing blood flow baselines.

Machine learning techniques may be used to identify and interpret patterns consistent with these events. Machine learning techniques can be used to distinguish events from the spectrum and thereby confirm the presence of a clot or other particle in the bloodstream. Machine learning techniques may further be used to interpret event patterns to characterize the size and frequency of different particles or clots in the bloodstream. Though fluid mechanics principles support the idea that there will be a detectable event when a clot or other particle is present in the blood stream, there is no closed-form solution for that event. In other words, though patterns for differential speed, preferred position of clots and other objects, and clustering tendencies exist, these patterns have not and cannot be determined definitely through observation and conventional mathematical techniques alone beyond highly simplified example scenarios.

Though the example embodiments described below concern blood clot detection, the techniques described herein may be used to detect any particles or objects in the bloodstream that pose a health risk. For instance these techniques may allow for detection of foreign or abnormal bodies in the bloodstream, such as cancer cells, and events signifying other health conditions. Therefore, a machine learning model is important to determining the existence of clots or other particles and identifying their characteristics. A machine learning model may be trained to effectively detect and characterize clots and other particles.

Figure 1:
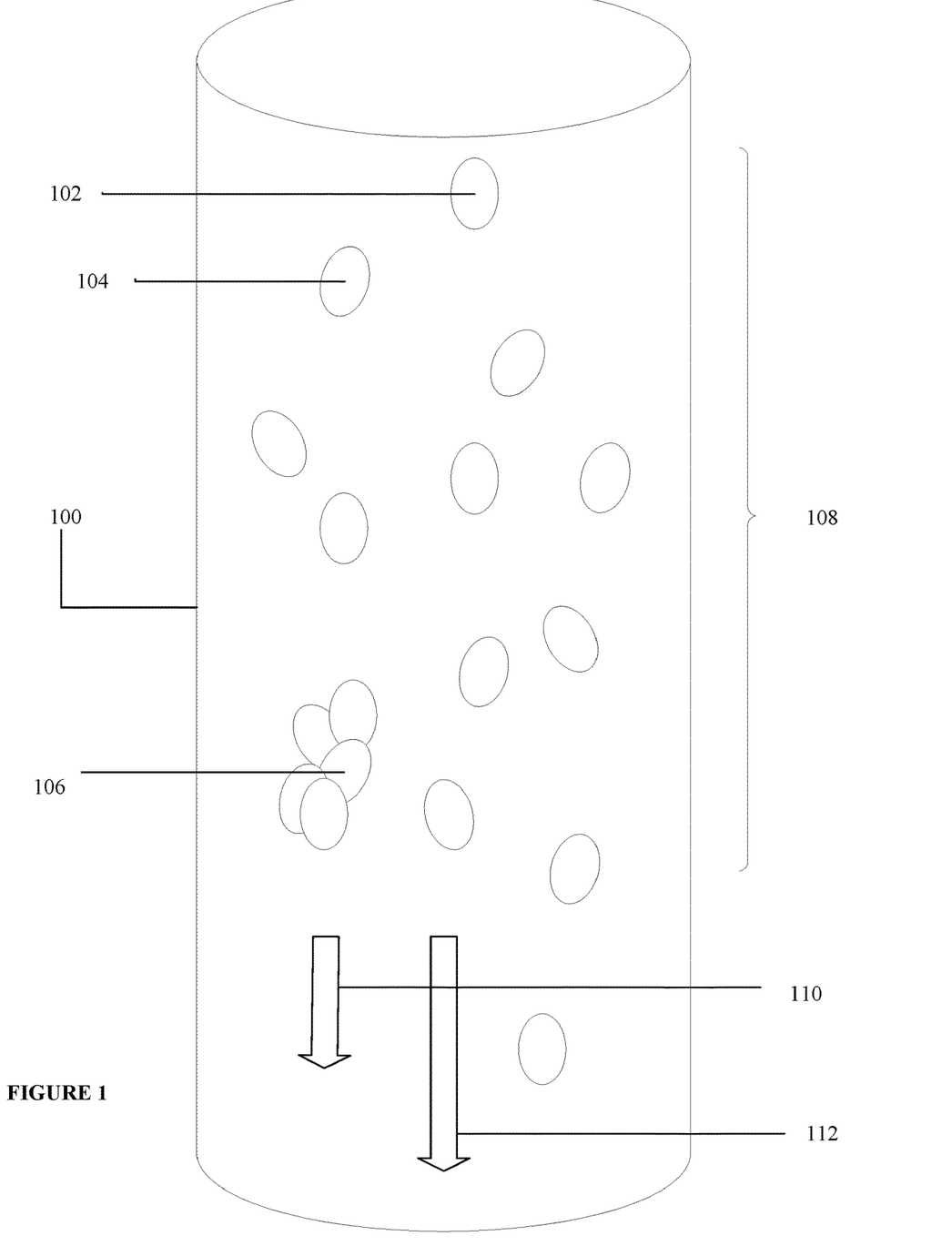
FIG. 1 is a diagram showing an example blood vessel segment through which a blood clot moves at a differential speed relative to the blood flow speed.

FIG. 1 is a diagram showing an example blood vessel segment through which a blood clot moves at a differential speed relative to the blood flow speed. The blood vessel segment 100 contains regular blood cells 102, 104 as well as a blood clot 106. In the segment 100, the blood cells 102, 104, and clot 106 together form a blood flow 108. This blood flow 108 may have a blood flow speed 112. The clot 106 may be moving within the blood flow 108. The clot 106 may move at a different speed 110 than the blood flow speed 112.

Figure 2:
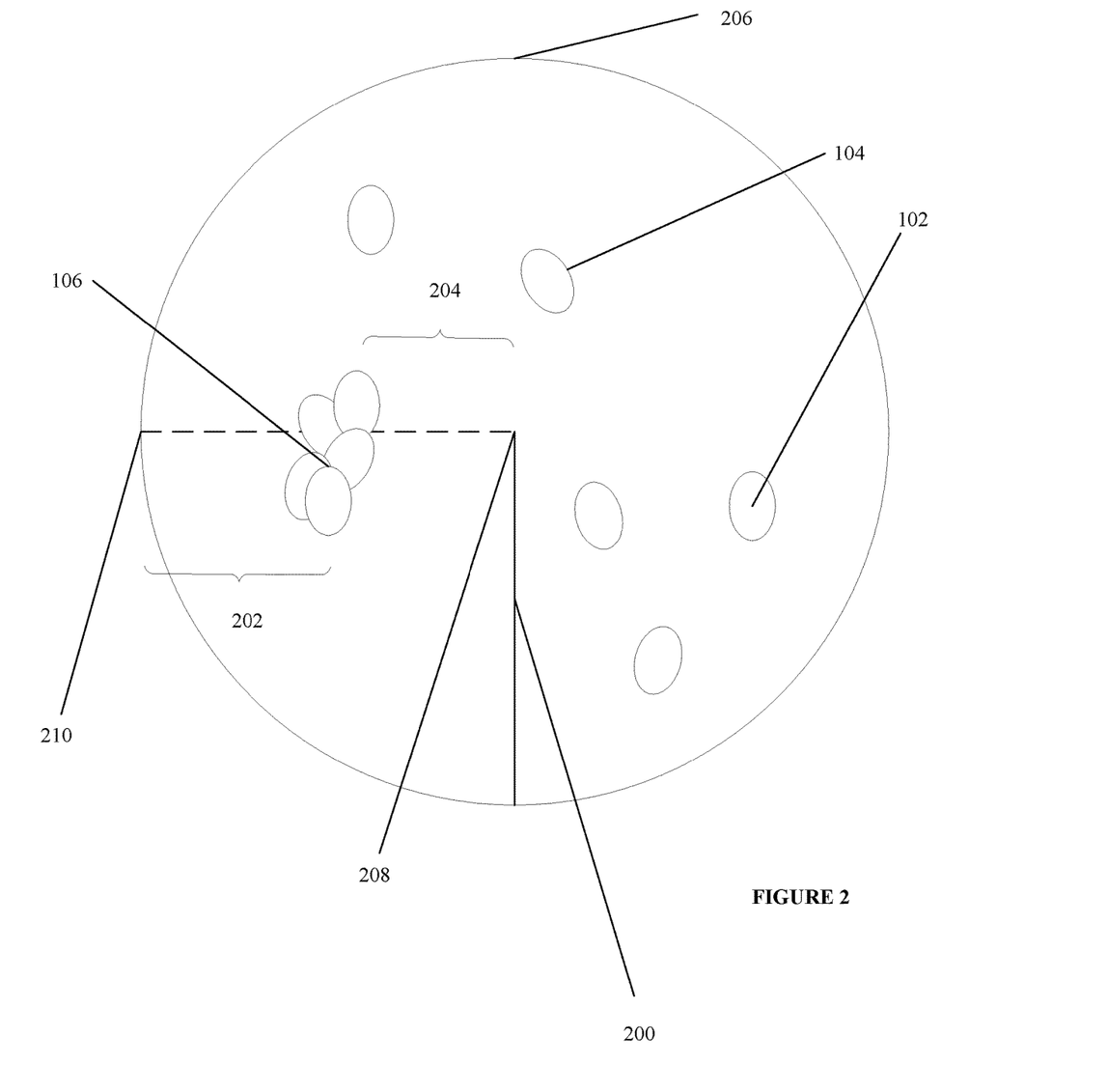
FIG. 2 is a diagram showing an example blood vessel cross section showing the relative position of a blood clot within the cross section.

FIG. 2 is a diagram showing an example blood vessel cross section showing the relative position of a blood clot within the cross section. The blood vessel cross section 206 contains regular blood cells 102, 104 as well as a blood clot 106. The blood vessel cross section has a radius 200. The blood clot 106 may occupy a particular position relative to the center 208 and the outer wall 210 of the blood vessel cross section 206. The position of the blood clot 106 may be described as the distance 202 along the radius 200 at which the blood clot 106 is relative to the outer wall 210 of the blood vessel cross section 206. The position of the blood clot 106 may also be described as the distance 204 along the radius 200 at which the blood clot 106 is relative to the center 208 of the blood vessel cross section 206.

Figure 3:
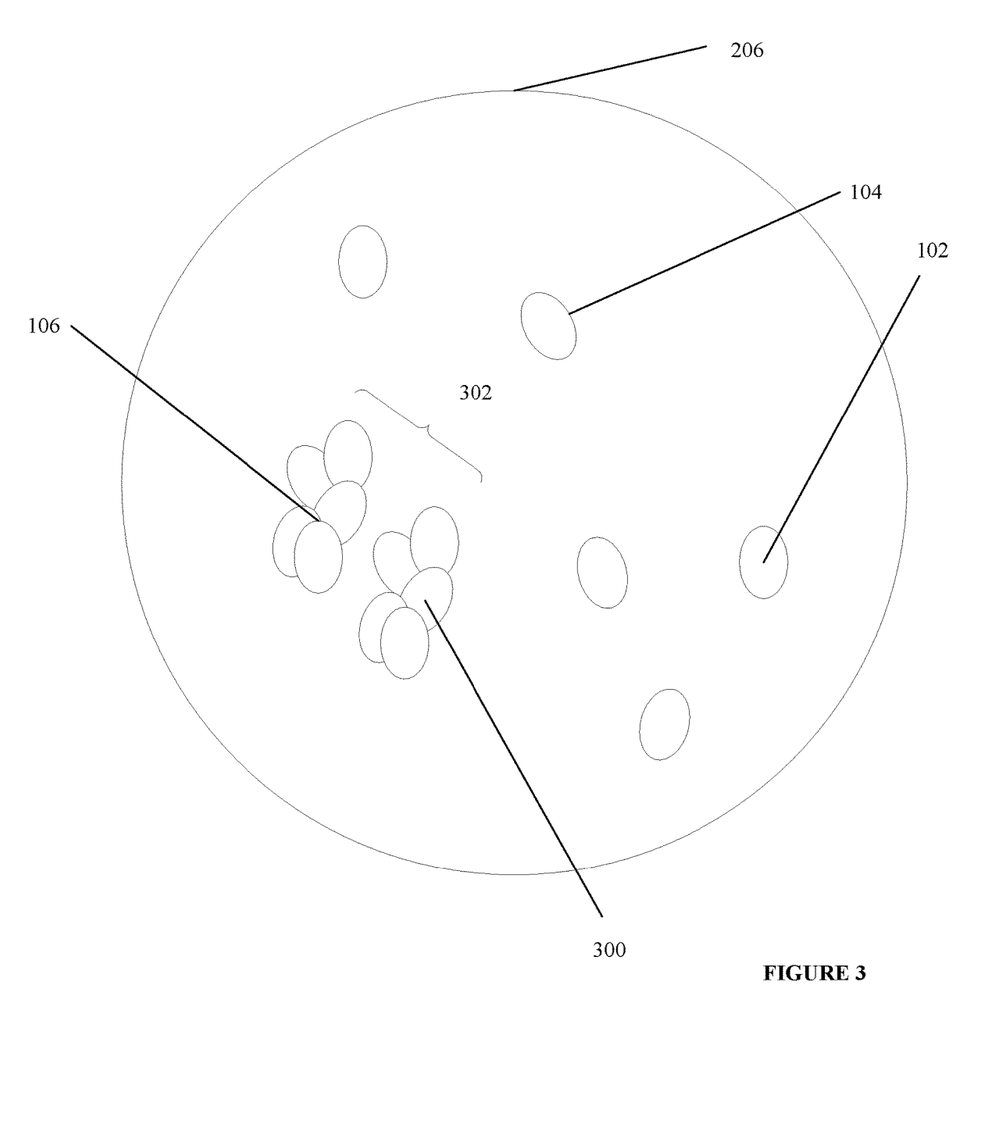
FIG. 3 is a diagram showing an example blood vessel cross section showing the relative position of blood clots to each other within the cross section.

FIG. 3 is a diagram showing an example blood vessel cross section showing the relative position of blood clots to each other within the cross section. The blood vessel cross section 206 contains regular blood cells 102, 104 as well as blood clots 106, 300. The relative position of the blood clots to each other may be expressed by a distance 302 between the two clots 106, 300. A blood vessel cross section 206 may also contain a plurality of blood clots which may each occupy positions relative to each other.

Figure 4:
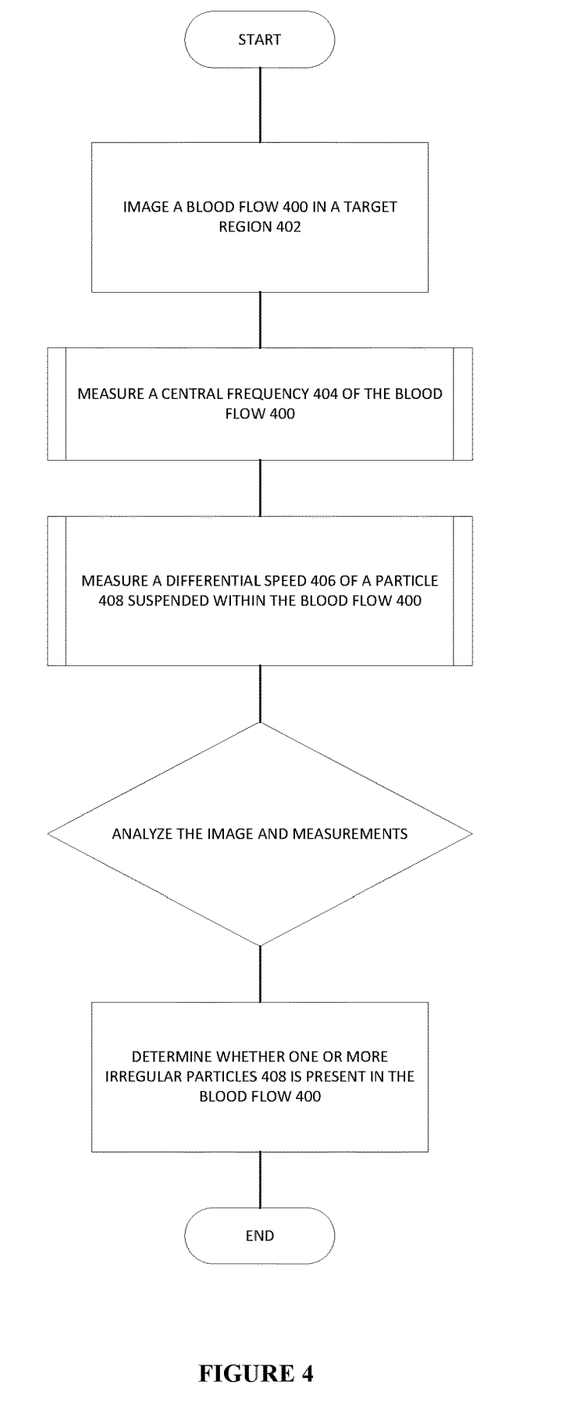
FIG. 4 is a flow diagram of an example of blood stream anomaly detection method.

FIG. 4 is a flow diagram of an example of a blood stream anomaly detection method. An ultrasound probe may be used to create an image sequence of a blood flow 400 in a target region 402 of a blood vessel. The target region 402 may be an area of the body in which measurements of the blood flow are desirable. For instance the target region 402 may be in a blood vessel in the arms or legs of a patient. The image may be created using different types of medical imaging technology. For example, color Doppler may be used to create the image sequence. From the image, a central frequency 404 of the blood flow 400 in the target region 402 of the blood vessel may be determined. The central frequency 404 is the Doppler frequency shift that corresponds to the bloodstream as a whole. A differential frequency 406 of one or more particles 408 suspended within the blood flow 400 may also be measured. Particles moving within the blood cell may have a different frequency than the surrounding blood flow. This frequency differential may be detectable from the image sequence of the blood flow.

The differential frequency 406 may be analyzed to determine properties of the blood flow and properties of any particle or particles suspended within the blood flow. For example, an analysis of the differential frequency 406 measured may reveal that an irregular particle is present in the blood flow 404. This irregular particle may be a blood clot.

Figure 5:
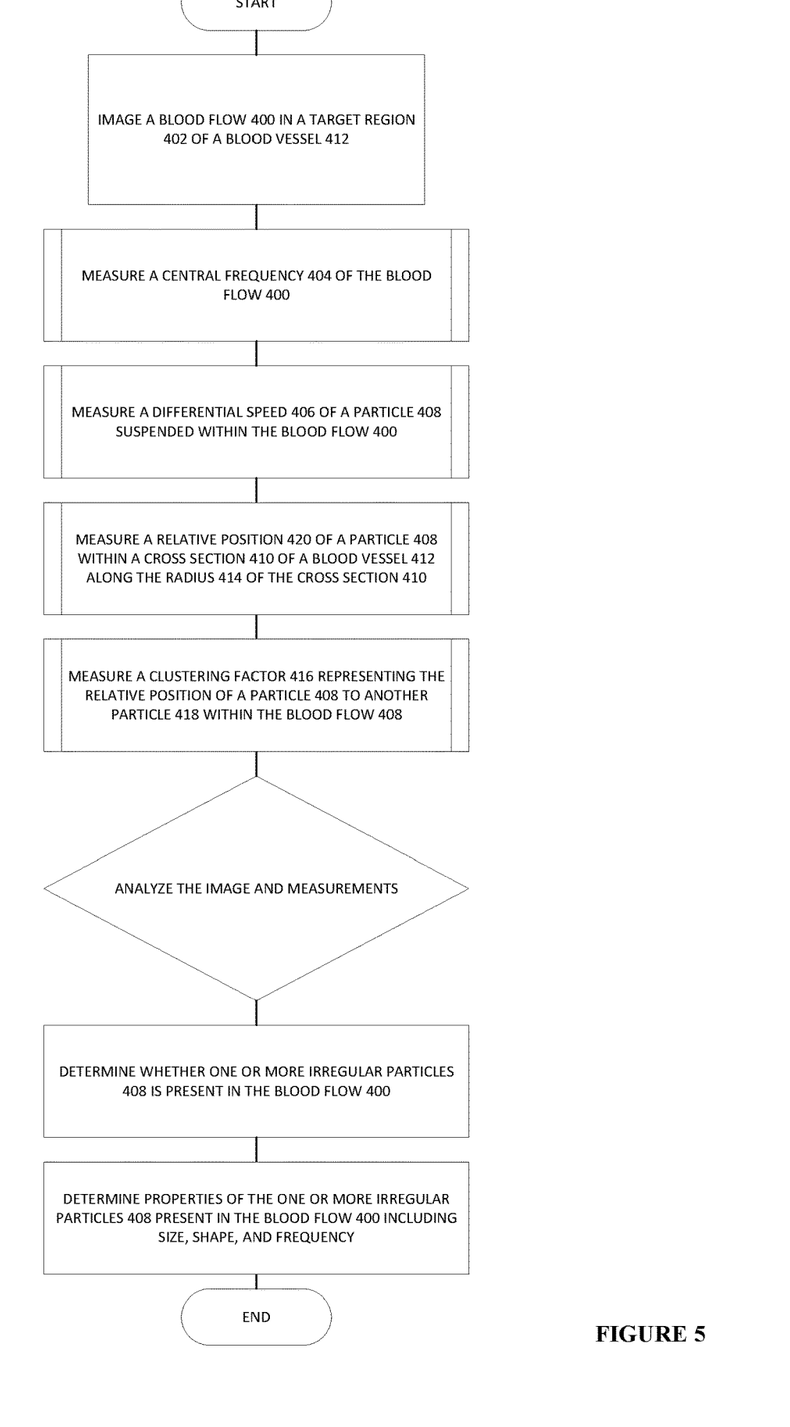
FIG. 5 is a flow diagram of an example of blood stream anomaly detection method.

FIG. 5 is a flow diagram of an example of a blood stream anomaly detection method. An ultrasound probe may be used to create an image sequence of a blood flow 400 in a target region 402 of a blood vessel 412. The target region 402 may be an area of the body in which measurements of the blood flow 400 are desirable. For instance the target region 402 may be in a blood vessel 412 in the arms or legs of a patient. The image may be created using different types of medical imaging technology. For example, color Doppler may be used to create the image sequence. From the image, a central frequency 404 of the blood flow 400 in the target region 402 of the blood vessel 412 may be determined. The central frequency 404 is the Doppler frequency shift that corresponds to the bloodstream as a whole.

Several properties of the blood flow 400 may be measured. These properties may reveal important information about the blood flow 400 which may reveal whether a medical risk is present. A differential frequency 406 of one or more particles 408 suspended within the blood flow 400 may also be measured. Particles moving within the blood cell may have a different frequency than the surrounding blood flow. This frequency differential may be detectable from the image sequence of the blood flow.

A relative position 420 of a particle 408 within a cross section 410 of a blood vessel 412 may be measured. Specifically, the position of a particle 408 along the radius 414 of the cross section 410 of the blood vessel 412 may be measured. For instance the distance between the particle 408 and the wall of the blood vessel 412 may be measured. Alternatively or additionally, the distance between the particle 408 and the center of the blood vessel 412 may be measured. Irregular particles in a blood flow 400, such as blood clots, may have a tendency to be suspended within certain areas in the blood flow 400. Therefore, the position of a detected particle 408 may provide information about the blood flow 400 that may correspond to a particular type of irregularity which may correspond to a particular type of health risk.

A clustering factor 416 may also be measured. The clustering factor may quantify the relative position of a particle 408 relative to another particle 418 within the blood flow 400. Some types of particles 408, 418 suspended within a blood flow 400 may have a propensity to be located close together within the blood flow 400. In one embodiment, the type of particle 408 may be a blood clot. Blood clots tends to cluster together within blood vessels. The measured clustering factor may provide information about the blood flow 400 which may correspond to a particular type of irregularity which may correspond to a particular type of health risk. For example, a measurement of many blood clots grouped very close together may reveal a significant risk of stroke.

The differential frequency 406, relative position 420, and clustering factor 416 may be analyzed to determine properties of the blood flow 400 and properties of any particle 408 or particles 408, 418 suspended within the blood flow 400. For example, an analysis of the differential frequency 406, relative position 420, and clustering factor 416 measured may reveal that an irregular particle is present in the blood flow 404. This irregular particle may be a blood clot.

The differential frequency 406, relative position 420, and clustering factor 416 may be further analyzed to determine the properties of a particle detected in the blood flow. For instance, these factors may reveal the size, shape, and/or frequency of a particle suspended in a blood flow. These factors may also correspond to a particular medical condition and/or the risk of a particular adverse medical event. For example, an analysis of the relative position of the blood clot within the blood vessel cross section may correspond to the risk of an adverse medical event, such as a stroke, or may reveal that the clot has reached a certain size. A further analysis of the clustering factor may likewise correspond to the risk of an adverse medical event, such as a stroke.

Figure 6:
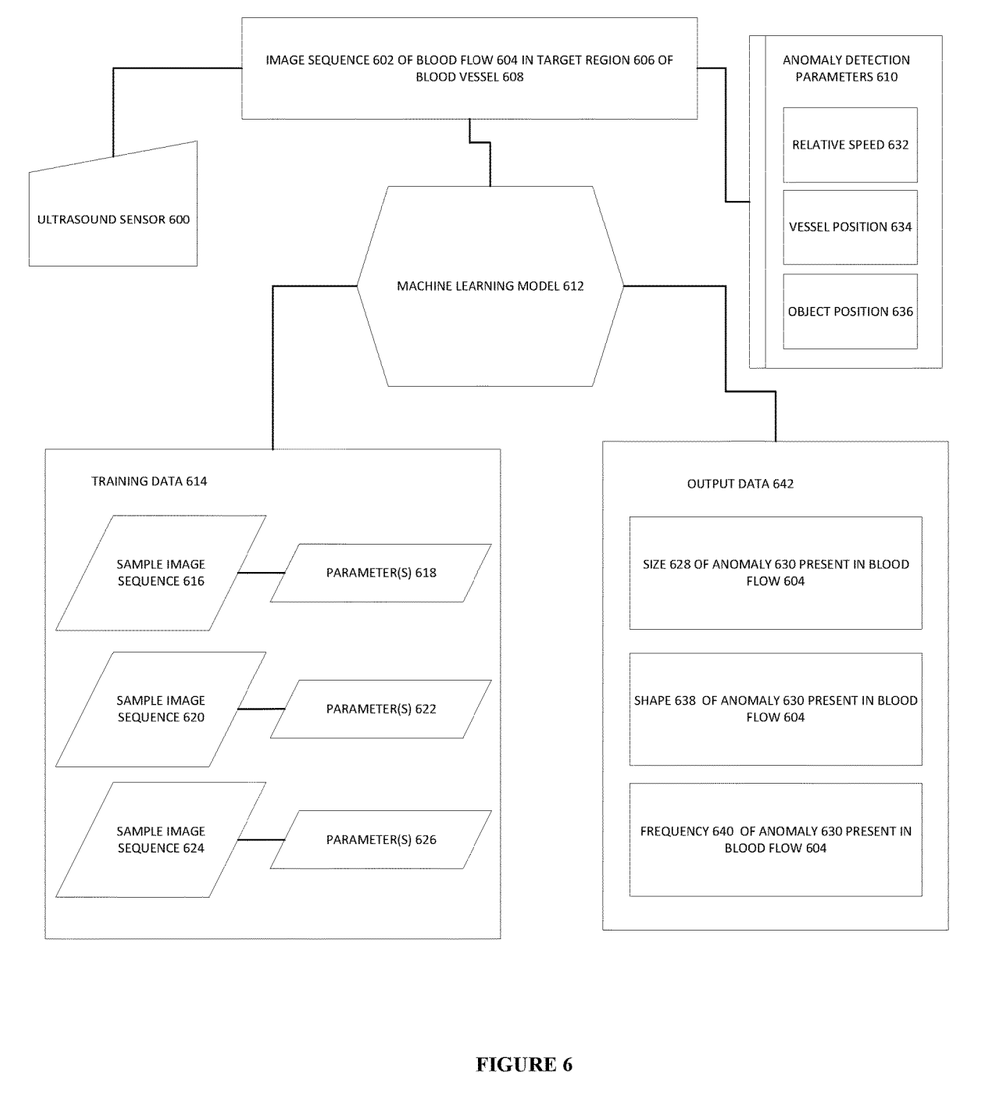
FIG. 6 is a diagram showing an example of a blood stream anomaly detection system.

FIG. 6 is a diagram showing an example of a blood stream anomaly detection system. A blood stream anomaly detection system may include an ultrasound sensor 600. The ultrasound sensor 600 may create an image sequence 602 of a blood flow 604 in a target region 606 of a blood vessel 608. A blood stream anomaly detection system may also include a set of anomaly detection parameters 610. A few example of relevant anomaly detection parameters may be relative speed 632 of a particle in the blood flow as compared to the speed of the blood flow itself, the relative position 634 of a particle in a blood flow, and the relative position 636 of a particle in a blood flow relative to other particles in the blood flow. The values of these parameters may reveal important information about a blood flow including the presence of an anomaly or irregular particle in the blood flow and the properties of any irregular particle, including the shape, size, and frequency of the irregular particle.

All of these anomaly detection parameters 610 may be determined from a high quality image sequence of a blood flow through a blood vessel. In an example embodiment, a high quality image sequence may be created using color Doppler techniques. The ultrasound sensor 600 may employ pulse-wave Doppler with short pulses to create the image sequence 602 of the blood flow 604 including the anomaly detection parameters 610.

A blood stream anomaly detection system may also include one or more sample datasets comprising training data 614. The sample datasets may be sample image sequences 616, 620, 624 of sample blood flows which are mapped to known parameters of interest 618, 622, 626. The known parameters of interest 618, 622, 626 may be known values anomaly detection parameters. For instance the known parameters 618, 622, 626 may correspond to known values for sizes, shapes, and/or frequencies of irregular particles detected in the sample image sequences. The irregular particles detected may be blood clots. The known parameters 618, 622, 626 may also correspond to set risk thresholds for particular health conditions. For example, known parameters 618, 622, 626 may correspond to samples in which blood clots with a greater than 50% chance of stroke are present.

A blood stream anomaly detection system may include a machine learning model 612. The machine learning model 612 may be trained using the training data 614. The trained machine learning model may then apply learned patterns to analyze the image sequence 602 of a blood flow 604 in a target region 606 of a blood vessel 608. The machine learning model may determine information about the blood flow 604 including the presence of any irregular particles in the blood flow and the properties of any detected irregular particles. The machine learning model may generate output data 642. The output data 642 may comprise values for properties of irregular particles detected in a blood flow. For example, the output data 642 may include a determined size 628 of an anomaly 630 present in the blood flow 604. The output data 642 may include a determined shape 638 of an anomaly 630 present in the blood flow 604. The output data 642 may include a determined frequency 640 of an anomaly 630 present in the blood flow 604.

In an example embodiment, the blood stream anomaly detection system of FIG. 6 may be specifically configured to detect blood clots in a blood flow. A blood clot detection and classification system may include an ultrasound sensor. The ultrasound sensor may create an image sequence of a blood flow in a target region. The blood clot detection and classification system may also include a set of blood clot detection parameters, including: (i) speed, wherein speed is the relative speed of a clot in the blood flow to the speed of the blood flow itself; (ii) vessel position, wherein vessel position is a relative position of the clot in the blood flow along the radius of the blood vessel; and (iii) clot position, wherein clot position is a relative position of the clot to other particles in the blood. An ultrasound sensor in a blood clot detection and classification system may employ pulse-wave Doppler with short pulses to create an image sequence of the blood flow including the blood clot detection parameters.

A blood clot detection and classification system may also include one or more sample datasets, wherein the sample datasets include image sequences of sample blood flows and corresponding known values for the blood clot detection parameters. A blood clot detection and classification system may also include a machine learning model, wherein the machine learning model is trained using the one or more sample datasets to, based on the blood clot detection parameters, detect the presence of a blood clot in the blood flow, determine the frequency of the blood clot in the blood flow, determine the diameter of the blood clot in the blood flow, and determine the shape of the blood clot in the blood flow.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method, comprising:
    capturing, using an ultrasound image sensor that employs pulse-wave Doppler with short pulses, an image sequence of a blood flow in a target region of a blood vessel;
    measuring, based on the image sequence,
        a central frequency corresponding to a first Doppler frequency shift of the blood flow as a whole viewed with the ultrasound image sensor in the target region of the blood vessel, and
        a second Doppler frequency shift corresponding to one or more objects suspended within the blood flow viewed with the ultrasound image sensor;
    determining, based on the central frequency and the second Doppler frequency shift, a differential in speed between the one or more objects suspended within the main blood flow and the blood flow as a whole;
    measuring, based on the image sequence, a relative position of the one or more objects within a cross section of the blood vessel by performing operations comprising:
        measuring a location of the one or more objects within the cross section of the blood vessel, and measuring a distance between the one or more objects and one or more other objects present in the blood flow in the cross section; and
    detecting, based on the differential in speed, the location, and the distance, that the one or more particles correspond to one or more anomalies present in the blood flow.

2. The method of claim 1, further comprising, determining, based on the differential in speed and the measured relative position, a size of the one or more anomalies present in the blood flow.

3. The method of claim 2, further comprising: confirming that at least one of the one or more anomalies has a diameter as small as 90 microns.

4. The method of claim 1, further comprising, determining, based on the differential in speed and the measured relative position, a shape of the one or more anomalies present in the blood flow.

5. The method of claim 1, wherein the ultrasound image sensor uses Color Doppler to construct the image sequence.

6. The method of claim 1, further comprising: training a machine learning model to detect the presence of an anomaly in a blood flow, the machine learning model trained using one or more collected data sets including sample image sequences of main blood flows in a target region and corresponding values for parameters of interest.

7. The method of claim 6, wherein one of the parameters of interest is the size of an anomaly in a controlled experiment.

8. The method of claim 6, wherein one of the parameters of interest is the frequency of an anomaly in a controlled experiment.

9. The method of claim 6, wherein the parameters of interest correspond to risk thresholds associated with certain health problems.

10. The method of claim 9, wherein one of the parameters of interest is the size of an anomaly corresponding to the size of a blood clot associated with a stroke.

11. The method of claim 6, wherein the machine learning model is a cognitive neural network.

12. The method of claim 1, further comprising: treating a medical condition corresponding to the one or more anomalies detected in the blood flow.

13. The method of claim 1, wherein:
    detecting that the one or more particles correspond to the one or more anomalies present in the blood flow comprises: detecting, using a trained machine learning model, based on the differential in speed, the location, and the distance, that the one or more particles correspond to the one or more anomalies present in the blood flow; and
    the machine learning model is trained using a dataset comprising a plurality of image sequences of sample blood flows and corresponding known values including: differentials in speed between objects suspended within the sample blood flows and the sample blood flows, locations of the objects suspended within the sample blood flows relative to blood vessels, and distances between the objects suspended within the sample blood flows and one or more other objects suspended within the sample blood flows.

14. The method of claim 13, further comprising, determining, using the trained machine learning model, based on the differential in speed and the measured relative position, a size of the one or more anomalies present in the blood flow.

15. The method of claim 14, further comprising: confirming, using the trained machine learning model, that at least one of the one or more anomalies has a diameter as small as 90 microns.

16. The method of claim 13, further comprising, determining, using the trained machine learning model, based on the differential in speed and the measured relative position, a shape of the one or more anomalies present in the blood flow.

17. The method of claim 13, further comprising, determining, using the trained machine learning model, based on the differential in speed and the measured relative position, a frequency of the one or more anomalies present in the blood flow.

18. The method of claim 13, wherein the machine learning model is a neural network.

19. The method of claim 1, wherein detecting that the one or more particles correspond to the one or more anomalies present in the blood flow comprises: detecting based on the differential in speed, the location, and the distance, and one or more risk thresholds for the one or more anomalies associated with a threshold differential in speed, a threshold location, or a threshold distance, that the one or more particles correspond to the one or more anomalies present in the blood flow.

20. The method of claim 1, wherein:
    the one or more anomalies are one or more blood clots;

detecting that the one or more particles correspond to one or more anomalies present in the blood flow comprises: detecting, using a trained machine learning model, based on the differential in speed, the location, and the distance, that the one or more blood clots are present in the blood flow; and the machine learning model is trained using a dataset comprising a plurality of image sequences of sample blood flows and corresponding known values including: differentials in speed between blood clots suspended within the sample blood flows and the sample blood flows, locations of the blood clots suspended with the sample blood flows relative to blood vessels, and distances between the blood clots suspended with the sample blood flows and one or more other blood clots suspended within the sample blood flows.

\* \* \* \* \*